(12) United States Patent
Yokawa et al.

(10) Patent No.: US 8,148,351 B2
(45) Date of Patent: Apr. 3, 2012

(54) ENTEROPATHY AMELIORATING COMPOSITION

(75) Inventors: Takeo Yokawa, Yokkaichi (JP); Noriyuki Ishihara, Yokkaichi (JP)

(73) Assignee: Taiyo Kagaku Co., Ltd., Yokkaichi-Shi (JP)

( * ) Notice: Subject to any disclaimer, the term of this patent is extended or adjusted under 35 U.S.C. 154(b) by 510 days.

(21) Appl. No.: 10/582,323

(22) PCT Filed: Aug. 26, 2004

(86) PCT No.: PCT/JP2004/012680
§ 371 (c)(1),
(2), (4) Date: Jun. 9, 2006

(87) PCT Pub. No.: WO2005/056022
PCT Pub. Date: Jun. 23, 2005

(65) Prior Publication Data
US 2007/0104760 A1 May 10, 2007

(30) Foreign Application Priority Data

Dec. 12, 2003 (JP) ................................. 2003-415496
Dec. 12, 2003 (JP) ................................. 2003-415502

(51) Int. Cl.
*A61K 31/70* (2006.01)

(52) U.S. Cl. ......................................... 514/54; 536/114

(58) Field of Classification Search ........................ None
See application file for complete search history.

(56) References Cited

U.S. PATENT DOCUMENTS

| | | | |
|---|---|---|---|
| 5,260,279 A | 11/1993 | Greenberg | |
| 5,614,501 A | 3/1997 | Richards | |
| 5,847,109 A * | 12/1998 | Garti et al. | 536/123 |
| 6,017,550 A | 1/2000 | Berk et al. | |
| 6,048,563 A * | 4/2000 | Swartz et al. | 426/573 |
| 6,087,092 A | 7/2000 | Richards | |
| 6,413,494 B1 | 7/2002 | Lee et al. | |
| 6,686,341 B1 | 2/2004 | Bijlsma et al. | |
| 6,706,295 B2 * | 3/2004 | Mehansho et al. | 426/72 |
| 6,730,661 B1 | 5/2004 | Kiliaan et al. | |
| 2002/0054923 A1 | 5/2002 | Suzuki et al. | |
| 2003/0064957 A1 | 4/2003 | Klyosov et al. | |
| 2003/0072770 A1 | 4/2003 | McAnalley et al. | |
| 2003/0162300 A1 | 8/2003 | Kunz et al. | |
| 2003/0166610 A1 | 9/2003 | Rochat et al. | |

FOREIGN PATENT DOCUMENTS

| | | |
|---|---|---|
| EP | 0 138 784 A2 | 4/1985 |
| EP | 1 172 041 A2 | 1/2002 |
| EP | 1 175 905 A1 | 1/2002 |
| EP | 1 186 297 A2 | 3/2002 |
| EP | 1 305 036 A2 | 5/2003 |
| EP | 1 303 632 B1 | 10/2004 |
| JP | 6-225734 A | 8/1994 |
| JP | 6-256196 A | 9/1994 |
| JP | 11-507406 T | 6/1999 |
| JP | 2000-232855 A | 8/2000 |
| JP | 2001-514523 A | 9/2001 |
| JP | 2001-292722 A | 10/2001 |
| JP | 2002-511051 A | 4/2002 |
| JP | 2002-154977 A | 5/2002 |
| JP | 2002-521346 A | 7/2002 |
| JP | 2002-218936 A | 8/2002 |
| JP | 2002-531510 T | 9/2002 |
| JP | 2002-539809 A | 11/2002 |
| JP | 2003-516757 A | 5/2003 |
| JP | 2003-289830 A | 10/2003 |
| JP | 2003-334045 A | 11/2003 |
| JP | 2003-534777 T | 11/2003 |
| WO | WO-96/03150 A1 | 2/1996 |
| WO | WO-98/39980 A1 | 9/1998 |
| WO | WO-00/57727 A1 | 10/2000 |
| WO | WO-01/33975 A1 | 5/2001 |
| WO | WO-02/07533 A2 | 1/2002 |
| WO | WO-02/076474 A1 | 10/2002 |

OTHER PUBLICATIONS

Parisi et al., "High-Fiber Diet Supplementation in Patients with Irritable Bowel Syndrome (IBS): A Multicenter, Randomized, Open Trial Comparison Between Wheat Bran Diet and Partially Hydrolyzed Guar Gum (PHGG)", Digestive Diseases and Sciences, vol. 47, No. 8, pp. 1697-1704, Plenum Publishing Corporation, Aug. 2002, XP-002527707.

De La Torre et al., "The use of Partially Hydrolyzed Guar Gum (PHGG)-containing formulas in the treatment of Inflammatory Bowel Disease (IBD)", Rivista Italiana Di Nutrizione Parenterale Ed Enterale, vol. 21, No. 3, pp. 105-111, Wichtig Editore, Milano, IT, Jan. 1, 2003, XP009116706.

Office Action dated Jan. 25, 2011 for Japanese Application No. 2005-516058.

Sakanaka et al., "The Physiological Functions as a Dietary Fiber of Partially Hydrolyzed Guar Gum", Bio Industry, vol. 18, No. 5, 2001, pp. 29-35.

* cited by examiner

*Primary Examiner* — Elli Peselev

(74) *Attorney, Agent, or Firm* — Birch, Stewart, Kolasch & Birch, LLP

(57) ABSTRACT

The present invention relates to a composition for preventing, ameliorating or treating a bowel disease, comprising galactomannan and/or arabinogalactan; a liquid food for preventing, ameliorating or treating a bowel disease, characterized in that the liquid food comprises a protein and galactomannan and/or arabinogalactan; and a composition for preventing, ameliorating or treating an irritable bowel syndrome, comprising degraded galactomannan.

11 Claims, 3 Drawing Sheets

ENTEROPATHY AMELIORATING COMPOSITION

TECHNICAL FIELD

The present invention relates to a composition for preventing, ameliorating or treating a bowel disease, and a food or a medicament, each comprising the composition. The present invention further relates to a liquid food for preventing, ameliorating or treating a bowel disease. The present invention further relates to a composition for preventing, ameliorating or treating an irritable bowel syndrome, and a medicament or a food, each comprising the composition.

BACKGROUND ART

In recent years, the number of patients with a bowel disease such as an inflammatory bowel disease or an irritable bowel syndrome is drastically increasing, as a disease incidental to civilization caused by change in eating habits or living environments.

An inflammatory bowel disease refers to a disease in which a mucosa of the intestine is led to cause inflammation by some cause such as ulcerative colitis (UC), Crohn's disease (CD) or intestinal Behçet disease, whereby resulting in erosion (sore) or ulcer.

Usually, the inflammation is considered to begin in the rectum near the anus, and thereafter spread toward the colon behind the rectum. Due to the inflammation which takes place in the intestine, a symptom such as diarrhea or mucous bloody stool (loose stool including blood, mucus and pus), fever or weight loss is produced. As conditions of the disease, amelioration (amelioration phase) and deterioration (active phase) are repeated in many cases, and the patient may learn to live with this disease for a long time in some cases. Especially, UC and CD are disease that have high frequency of incidence, and are intractable, and apt to be extended, thereby making it difficult to be clinically treated. Fundamental therapies for UC and CD have not been established at present, and nutritional therapy (total parenteral nutrition therapy, enteral nutrition therapy, alimentotherapy) and pharmacotherapy (sulfasalazine, a sulfa drug of 5-ASA (mesalazine), a steroid drug such as prednisolone, or an immunosuppressant such as azathioprine is used stepwise depending on the stage of the disease) are employed (for example, see the group of "Research and Study on Intractable Inflammatory Bowel Disorder," Ministry of Health, Labor and Welfare, Annual Report in the fiscal year Heisei 13 (2001), p.54).

UC was accepted as a specified disease in 1975, and CD in 1976. The number of registered beneficiaries of the specified disease for UC is said to be about 70,000 and that for CD is about 20,000, and the number of the patients tends to increase in recent years ("Ministry of Health and Welfare, Department of Health and Medicine, Section of Measure for AIDS and Disease, Subsection of Intractable Diseases").

The number of patients with intestinal Behçet disease is smaller than that of the patients with UC and CD. However, the intestinal Behçet disease is intractable, and pharmacotherapy, nutritional therapy and surgical therapy similar to those in UC and DC are implemented.

Majority of the other inflammatory bowel diseases are basically curable with internal treatment, and nutritional therapy (fasting, dietary restriction, elemental diet, high-calorie parenteral nutrition), pharmacotherapy (administration of an antibacterial drug), or the like are conducted depending on the symptoms (see, for example, *Matsushita Medical Journal*, 39: 1-14, 2000).

Although studies on an inflammatory bowel disease have been carried on by the group of research and study on specified diseases of Ministry of Health, Labor and Welfare, the causation of why the diseases arise is yet to be clearly elucidated.

As a recent prominent theory, it is suggested that abnormality in immunity such as autoimmune mechanism may be the causation. Human body is provided with a mechanism of excluding a foreign substance upon its invasion from the external (immune function). This immune function also acts in the intestine. When this immune function becomes abnormal, the mechanism regards its own mucosa as a foreign substance, and attacks and damages the mucosa. As a result, inflammation is generated in the mucosa. It is considered that when immune function is abnormally activated for excluding a foreign substance, a leukocyte acts excessively, and the leukocyte keeps releasing a substance for supposedly inherently processing a foreign substance, thereby causing a continuous inflammation.

However, this immune theory is not decisive. While this theory is prominent as a system explaining why inflammation is caused, the mechanism for the onset of inflammatory bowel diseases, namely how abnormality in immune function is caused, is not explicitly elucidated. Therefore, fundamental therapy has not yet been established.

Therefore, development in various therapies for inflammatory bowel diseases has been advanced at present. Unfortunately, a therapy which is capable of completely curing the diseases is yet to be found. Accordingly, prevention or treatment of an inflammatory bowel disease is an important problem.

For example, in the alimentotherapy, if a therapy is carried on for a long time, an individual may be subject to lack of nutritional balance, thereby making the symptoms more serious in some cases. In addition, the pharmacotherapy has some disadvantages such as the drug has a risk for causing a side effect in addition to the therapeutic effect. When the inflammatory bowel disease is serious, a surgical operation may be necessitated in some cases.

Among various diseases of digestive apparatus, an irritable bowel syndrome (IBS) is one of the diseases most frequently found. It is said that about 20 to 30% of the patients who seek medical attention due to abnormality in bowel movement suffer from irritable bowel syndrome in Japan. As to the age group, the irritable bowel syndrome is often found in their twenties or fifties for women, and their thirties to forties for men.

Main symptoms of IBS include abnormality in bowel movement, abdominal pain and abdominal discomfort. Among them, in the abdominal pain, the site of pain is not necessarily the same, and the degree of pain varies from slight pain to serious pain. Also, one of the features of the syndrome resides in alleviation of the abdominal pain by defecation.

As to the IBS, stress is regarded as one of the causes thereof, because organs and nerves are associated to each other. The actions of organs are governed by autonomic nerves, and the autonomic nerves act according to a signal from the hypothalamus of the brain. When information serving as a stress enters into the brain from the external, the hypothalamus reacts to the information, thereby making it difficult to deliver a proper signal to the autonomic nerves, which in turn cause disturbance of the action of the organs.

For the patients with IBS as described above, instruction, method of treatment or the like, such as regaining normal bowel-movement habit by leading a regular life; relieving stress by engaging in sports, hobbies or the like; receiving counseling from an expert; implementing pharmacotherapy with an analgesic, an agent for ameliorating motor function of digestive apparatus, a tranquilizer, a herbal medicine; or the like has been tried (see, Sasaki, D. and Sudo, T., *G.I. Research*, 7: 3-9, 1999).

DISCLOSURE OF THE INVENTION

As described above, a therapy which is capable of fundamentally curing a bowel disease such as an inflammatory bowel disease is yet to be found at present, and prevention or treatment of a bowel disease such as an inflammatory bowel disease is an important problem. In addition, this disease gives a serious pain mentally and physically to patients with an inflammatory bowel disease for the above-mentioned reasons. Therefore, development of a composition for ameliorating a bowel disease which is capable of easily ameliorating these diseases while the seriousness of the diseases is slight is desired.

On the other hand, for an irritable bowel syndrome, the pharmacotherapy as described above or the like is implemented. However, it is difficult to continue the implementation of the therapy due to the disadvantage of a side effect. Also, the mechanism of the syndrome is not explicitly elucidated, so that a fundamental therapy is yet to be established.

Therefore, an object of the present invention is to provide a highly safe composition for preventing, ameliorating or treating a bowel disease, which is free from a disadvantage such as a side effect.

A still more object of the present invention is to provide a highly safe liquid food for preventing, ameliorating or treating a bowel disease, which is free from a disadvantage such as a side effect and capable of ameliorating a bowel disease.

A still more object of the present invention is to provide a composition for preventing, ameliorating or treating an irritable bowel syndrome, which is free from a disadvantage such as a side effect.

Specifically, the gist of the present invention relates to:

[1] a composition for preventing, ameliorating or treating a bowel disease, comprising galactomannan and/or arabinogalactan;

[2] the composition according to the above [1], wherein the bowel disease is an inflammatory bowel disease;

[3] the composition according to the above [1] or [2], wherein the composition comprises degraded galactomannan as the galactomannan;

[4] a food or a medicament comprising the composition as defined in any of the above [1] to [3];

[5] a liquid food for preventing, ameliorating or treating a bowel disease, comprising a protein and galactomannan and/or arabinogalactan;

[6] the liquid food according to the above [5], wherein the bowel disease is an inflammatory bowel disease;

[7] the liquid food according to the above [5] or [6], wherein the protein is one or more kinds of proteins selected from the group consisting of a soy protein, a milk protein, a yolk protein, an albumen protein, a wheat protein and a degraded product thereof;

[8] the liquid food according to any of the above [5] to [7], wherein the liquid food comprises degraded galactomannan as the galactomannan;

[9] a composition for preventing, ameliorating or treating an irritable bowel syndrome, comprising galactomannan;

[10] the composition according to the above [9], wherein the composition comprises degraded galactomannan as the galactomannan; and

[11] a medicament or a food, each comprising the composition as defined in the above [9] or [10].

BEST MODE FOR CARRYING OUT THE INVENTION

Figure 1:
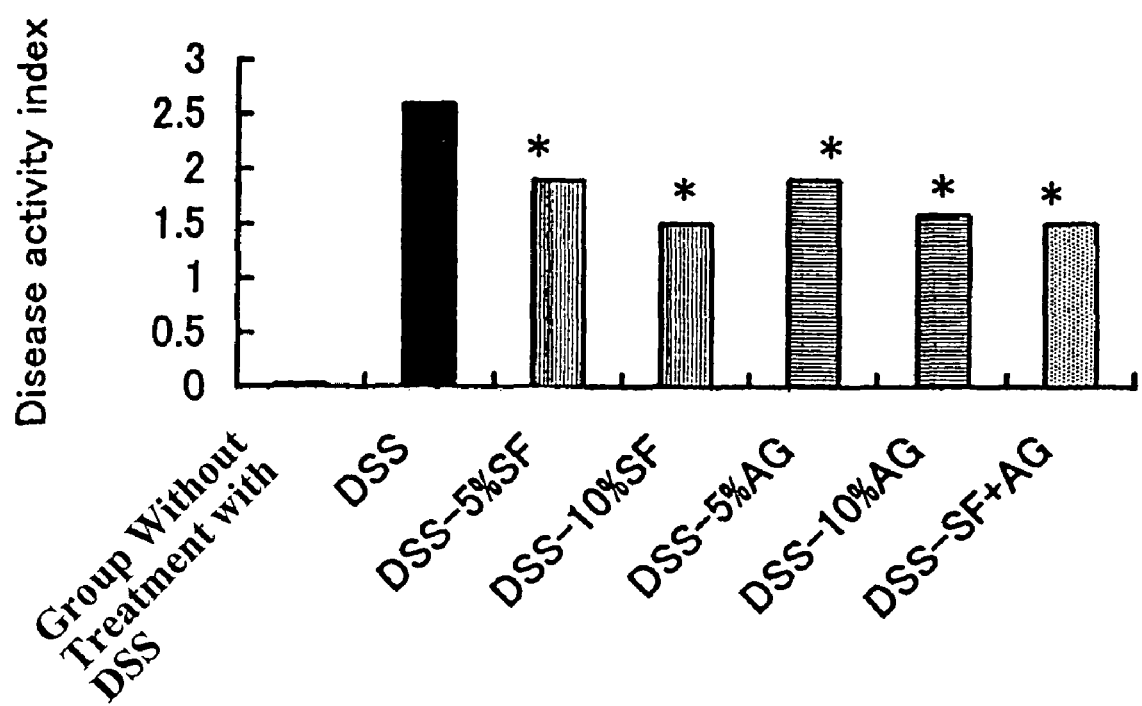
FIG. 1 is a graph showing comparison of disease activity index in each feed group.

First, a first embodiment of the present invention will be explained.

One of the great features of the composition for preventing, ameliorating or treating a bowel disease of the present embodiment resides in that the composition comprises galactomannan and/or arabinogalactan.

The present embodiment is based on the findings by the present inventors that galactomannan and arabinogalactan which are known to confer preferred physical properties to various industrially manufactured articles surprisingly have an effect of preventing, ameliorating or treating a bowel disease, especially an inflammatory bowel disease.

An inflammatory bowel disease refers to a disease in which some cause such as ulcerative colitis, Crohn's disease or intestinal Behçet disease causes inflammation in mucosa of a large intestine, whereby resulting in erosion (sore) or ulcer. A method for evaluating the inflammation is not limited particularly, and the evaluation of disease activity index, the activity of myeloperoxidase (MPO), which is an inflammation marker, the activity of TNF-α, which is an inflammatory cytokine, or the like has been known. These methods for evaluation are not limited particularly, and a method of Cooper et al. can be employed for disease activity index (*Lab. Invest.*, 69, 238-49, 1993), a method of Grisham et al. for MPO activity (*Am. J. Physiol.*, 252: G567-G74, 1986), and a sandwich assay for TNF-α activity.

The composition of the present embodiment, when administered to a model mouse for an inflammatory bowel disease such as colitis, not only prevents, ameliorates or treats an inflammatory bowel disease, but also significantly lowers the activity of myeloperoxidase, which is an inflammation marker, and the activity of TNF-α. Specifically, the composition of the present embodiment is capable of preventing, ameliorating or treating an inflammatory bowel disease even when administered to human, and the evaluation thereof can be carried out by determining the activity of myeloperoxidase, which is an inflammation marker, and the activity of TNF-α.

The galactomannan in the present embodiment includes natural mucous materials such as guar gum, locust bean gum, tara gum, cassia gum, sesbania gum and fenugreek. The galactomannan is preferably guar gum, locust bean gum and sesbania gum, and more preferably guar gum and locust bean gum, from the viewpoint of ease in ingestion and effects. Commercially available galactomannan includes NEOSOFT G (manufactured by Taiyo Kagaku Co., Ltd.), NEOSOFT L (manufactured by Taiyo Kagaku Co., Ltd.) and the like.

In the present embodiment, the galactomannan may be used as it is. It is preferable to use degraded galactomannan prepared by hydrolyzing galactomannan, from the viewpoint of suppressing increase in viscosity of the composition. In other words, in the present embodiment, the galactomannan includes degraded galactomannan. The degraded galactomannan can be obtained by hydrolyzing the above-mentioned galactomannan used as a raw material to lower the molecular weight of the galactomannan by a known method. When degraded galactomannan is prepared, each of the above-mentioned galactomannan can be used alone or in a mixture of two or more kinds thereof.

Methods of hydrolysis include, but not particularly limited to, for example, enzymolysis, acidolysis and the like. Enzymolysis is preferable, from the viewpoint of being capable of evenly sizing the molecular weight of the degraded products.

The enzyme used for enzymolysis is not limited particularly, and the enzyme may be commercially available products, those derived from natural products, or those obtained by known recombinant techniques, as long as the enzyme is capable of hydrolyzing mannose straight chain. the enzyme is preferably β-mannanase derived from a bacterium belonging to *Aspergillus, Rhizopus* or the like, from the viewpoint of enhancing the degradation efficiency.

The conditions for the above-mentioned enzymolysis of galactomannan cannot be described unconditionally because the conditions vary depending on the enzyme used. The conditions include, for example, conditions of carrying out a reaction at 10° to 80° C. for about 1 to about 75 hours in the presence of the enzyme in an amount of from 0.1 to 20 parts by weight based on 100 parts by weight of the raw material galactomannan, in a buffer suitable for the enzyme used.

The conditions for acidolysis include, but not particularly limited to, for example, conditions of carrying out a reaction at 90° to 100° C. for about 1 to about 40 hours in any solvent having a pH of from 1 to 4.

By the procedures described above, degraded galactomannan is obtained. The resulting degraded product can be used as it is, or can be used after being washed with water or the like if desired. Commercially available products can also be used. The commercially available products include, for example, SUNFIBER. (manufactured by Taiyo Kagaku Co., Ltd.), FIBERON (manufactured by DAINIPPON PHARMACEUTICAL CO., LTD.) and the like.

Furthermore, it is preferable that the degraded galactomannan used in the present embodiment has a viscosity of 50 mPa·s or less, more preferably 20 mPa·s or less, and even more preferably 10 mPa·s or less, as determined by its 0.5(w/v) % aqueous solution with a B Type Viscometer at 25° C.

The galactomannan used in the present embodiment preferably has an average molecular weight of 2,000 to 1,000,000. When the average molecular weight is 2,000 or more, the effects of the present embodiment are satisfactorily exhibited. On the other hand, when the average molecular weight is 1,000,000 or less, the viscosity is not too high, so that a disadvantage upon processing the galactomannan into a food is less likely to be caused. Therefore, the average molecular weight of the galactomannan is preferably from 2,000 to 1,000,000, and more preferably from 8,000 to 100,000.

When the degraded galactomannan is used in the present embodiment, the molecular weight of the degraded galactomannan is preferably from 2,000 to 100,000, more preferably from 8,000 to 50,000, and even more preferably from 15,000 to 25,000, from the viewpoint of excellent exhibition of the desired effects and usefulness.

The average molecular weight can be obtained, for example, by subjecting galactomannan or degraded galactomannan to high-performance liquid chromatography (column manufactured by YMC Co., Ltd., YMC-Pack Diol-120) using polyethylene glycols (molecular weights: 2,000, 20,000 and 200,000) as molecular weight markers to obtain the molecular weight distribution, numerically expressing the molecular weight distribution by applying the molecular weight distribution to the calibration curve obtained from the molecular markers, and averaging the resulting values.

The arabinogalactan in the present embodiment is not limited particularly, and those prepared by subjecting a root of a Japanese larch to a warm-water extraction, purification of the extract and spray-drying to powder, such as ARABINOGALACTAN LF manufactured by Taiyo Kagaku Co., Ltd., can be used. The average molecular weight thereof is not limited particularly, and those falling within the range of from 2,000 to 500,000 can be preferably used. Those having an average molecular weight of 2,000 or more are less likely to cause a disadvantage in taste, and those having an average molecular weight of 500,000 or less rarely have a problem in giving taste and mouth feel. Here, the average molecular weight can be determined using a method in the same manner as in the above-mentioned galactomannan.

The content of the galactomannan is, when the galactomannan is used alone in the composition for preventing, ameliorating or treating a bowel disease of the present embodiment, preferably from 0.1 to 100% by weight, and more preferably from 1 to 50% by weight of the composition, from the viewpoint of ease in obtaining the effect of preventing, ameliorating or treating an inflammatory bowel disease and ease in use. The content of arabinogalactan is, when arabinogalactan is used alone, preferably from 0.1 to 100% by weight, and more preferably from 1 to 50% by weight of the composition, from the viewpoint of ease in obtaining the effect of preventing, ameliorating or treating an inflammatory bowel disease, and ease in use. The content of the galactomannan and the arabinogalactan is, when galactomannan and arabinogalactan are used together, preferably from 0.1 to 100% by weight, and more preferably from 1 to 50% by weight of the composition, from the viewpoint of ease in obtaining the effect of preventing, ameliorating or treating an inflammatory bowel disease, and ease in use, and the composition ratio is not limited particularly, so far as the effects of the present embodiment are exhibited.

To the composition of the present embodiment, other sugars, a dietary fiber, a lipid, an amino acid or a protein can be added in addition to the galactomannan and the arabinogalactan, and a substance having other functions, such as lactic acid bacteria, vitamin or mineral can be optionally further added thereto.

It is preferable that the composition of the present embodiment is continuously ingested in an amount of preferably from 1 to 70 g, and more preferably from 5 to 20 g per day per adult, from the viewpoint of suppression and treatment of an inflammatory bowel disease.

The present embodiment further provides a food, a medicament or a feed, each comprising the above-mentioned composition.

The food of the present embodiment includes, for example, a beverage, a cookie, a snack, a milk product and the like. The food of the present embodiment can be prepared by, for example, adding the composition of the present embodiment to an already made food, or by adding the composition of the present embodiment to a food raw material in advance during the preparation of these foods or mixing the composition and a food raw material together during the preparation step.

The content of the above-mentioned composition in the food of the present embodiment is not limited particularly, so far as the desired object of the food is accomplished and the desired effects of the present embodiment are exhibited.

The medicament of the present embodiment may contain a component conventionally used in a medicament, such as an excipient, a binder, a disintegrant, a lubricant, a flavor, an extender, or a coating agent, in addition to the above-mentioned composition.

The form of the medicament of the present embodiment may be, for example, in the form of any of a solution, a suspension, a powder, a solid mold and the like, and the preparation form includes a tablet, a capsule, a powder, a granule, a drinkable preparation, an injection, a patch, an ointment and the like. These medicaments are prepared in the same manner as in a usual medicament, except that the above-mentioned composition is added thereto.

The dose of the medicament for obtaining the desired effects of the present embodiment may be such that a composition for preventing, ameliorating or treating a bowel disease is preferably from 1,000 to 70,000 mg/day, and more preferably from 5,000 to 20,000 mg/day. However, since there are individual differences (kinds or degree of symptoms, age and the like), the dose in the present embodiment is not limited to the above range. The dose may be properly set specifically for each case, so as to obtain the desired effects of the present embodiment.

The method for administration of the medicament of the present embodiment includes, but not limited particularly to, oral administration, enteral administration and the like. More preferably, the method is oral administration.

The feed of the present embodiment can be prepared by, for example, adding the composition of the present embodiment to an already made feed, or alternatively adding the composition of the present embodiment to a feed raw material in advance during the preparation of these feeds, or mixing the composition and a feed raw material together during the preparation step.

The content of the above-mentioned composition in the feed of the present embodiment is not limited particularly, so far as the given object of the feed is accomplished and the desired effects of the present embodiment are exhibited.

The present embodiment further provides a method of using the above-mentioned composition, food or medicament for preventing, ameliorating or treating a bowel disease, especially an inflammatory bowel disease. The present embodiment further provides a method for preventing, ameliorating or treating a bowel disease, especially an inflammatory bowel disease, using the above-mentioned composition, food or medicament.

Next, a second embodiment of the present invention will be explained.

One of great features of the liquid food for preventing, ameliorating or treating a bowel disease of the present embodiment has a great feature that the liquid food comprises a protein and galactomannan and/or arabinogalactan.

The present embodiment is based on the findings of the present inventors that galactomannan and arabinogalactan which are known to confer physical properties preferable in various industrially manufactured articles surprisingly have an effect of preventing, ameliorating or treating a bowel disease, especially an inflammatory bowel disease, so that mucosal disorder due to inflammation such as an inflammatory bowel disease can be alleviated by using galactomannan and/or arabinogalactan in combination with a protein such as a soy protein or a milk protein which is known to have various physiological activities such as prevention from arteriosclerosis or hypertension, or action of lowering "the bad cholesterol" (low-density lipoprotein cholesterol).

In the second embodiment of the present invention, the liquid food of the present embodiment relates to a novel liquid food which is capable of supplementing one's diet by oral or enteral ingestion and effective in prevention, amelioration or treatment of an inflammatory bowel disease of a tested individual.

The viscosity of the liquid food of the present embodiment is in a range of desirably from 10 to 100 mPa·s, and especially preferably from 12 to 50 mPa·s, from the viewpoint of maintaining the effects and improving compliance of a patient.

The protein used in the liquid food of the present embodiment includes, for example, a soy protein, a milk protein, a yolk protein, an albumen protein, a fish-and-shell protein, a seaweed protein, a nut protein, a wheat protein, and a degraded product thereof. The protein is preferably a soy protein, a milk protein and a degraded product thereof, and more preferably a degraded soy protein and a degraded milk protein, from the viewpoint of taste. Here, the protein may be a mixture of amino acids based on the components of the protein.

The degraded product of a protein is obtained by hydrolyzing the above-mentioned protein used as a raw material by a known method, to lower the molecular weight of the protein. When a degraded product of a protein is prepared, the above-mentioned protein can be used alone separately or in combination of two or more kinds thereof.

Methods of hydrolysis include, but not particularly limited to, for example, enzymolysis, acidolysis and the like. From the viewpoint that the molecular weight of the degraded products can be easily evenly sized, enzymolysis is preferable.

The enzyme used for enzymolysis may be, but not particularly limited to, a commercially available product, one derived from natural products, or one obtained by known recombinant techniques, as long as the enzyme is capable of hydrolyzing a peptide bond. From the viewpoint of enhancing the degradation efficiency, the enzyme is preferably a proteinase or a peptidase derived from a bacterium belonging to *Aspergillus*, a bacterium belonging to *Bacillus* or the like.

By the procedures described above, a degraded product of a protein can be obtained. A commercially available product may also be used. The commercially available product includes, for example, NIKKA MILKY (manufactured by Nikka Fats & Oils Co., Ltd.), which is a degraded product of a soy protein, CASEIN PHOSPHOPEPTIDE (CPP) (manufactured by MEIJI SEIKA KAISHA, LTD.), which is a degraded product of a milk protein, YOLKLATE (manufactured by Taiyo Kagaku Co., Ltd.), which is a degraded product of a yolk protein, SUNKIRARA (manufactured by Taiyo Kagaku Co., Ltd.), which is a degraded product of an albumen protein, AMINOMARINE (manufactured by SAKAMOTO KANPOH PHARMACEUTICALS INC.), which is a degraded product of a protein derived from mackerel, MAINICHI KAISAI NORI PEPTIDE (manufactured by SHIRAKO co., ltd.), which is a degraded product of a protein derived from laver, BIOMARINE (manufactured by Nihon Bussan), which is a degraded product of a protein and collagen, each derived from an albumen, milk, a soybean, fish and shell, and nuts, and the like.

When a degraded product of a protein is used in the present embodiment, the average molecular weight is preferably 500 or more, and more preferably 1000 or more, from the viewpoint of taste.

The average molecular weight can be obtained, for example, by subjecting the degraded product of a protein to high-performance liquid chromatography (column manufactured by YMC Co., Ltd., YMC-Pack Diol-120) using pullulan (molecular weights: 500, 1,000 and 2,000) as molecular weight markers to obtain the molecular weight distribution, applying the molecular weight distribution to a calibration curve obtained from the molecular markers to numerically express the molecular weight, and averaging the obtained values.

The content of the protein in the liquid food of the present embodiment is preferably from 0.1 to 90% by weight, and more preferably from 10 to 30% by weight in the liquid food, from the viewpoint of satisfactorily exhibiting the effect of the present embodiment and suppressing lowering of taste.

The galactomannan and the arabinogalactan in the present embodiment are similar to those in the above-mentioned first embodiment.

When a protein and galactomannan are used, or a protein and arabinogalactan are used in the liquid food of the present embodiment, the contents of the both the galactomannan and the arabinogalactan are each preferably from 0.1 to 40% by weight, and more preferably from 0.8 to 20% by weight in the liquid food, from the viewpoint of ease in obtaining the effect of preventing, ameliorating or treating a bowel disease, especially an inflammatory bowel disease, and ease in use. The total content of the galactomannan and the arabinogalactan, when used together, is preferably from 0.1 to 40% by weight, and more preferably from 0.8 to 20% by weight in the liquid food, from the viewpoint of ease in obtaining preventing, ameliorating or treating a bowel disease, especially an inflammatory bowel disease, and ease in use.

The liquid food of the present embodiment can be prepared by homogenously mixing a protein and galactomannan and/or arabinogalactan together with water. Upon the preparation, an emulsifying agent can be compounded thereto if needed. The emulsifying agent includes, for example, a glycerol fatty acid ester, a sucrose fatty acid ester, stearoyl calcium lactate, a sorbitan fatty acid ester, a propylene glycol fatty acid ester, or lecithin, saponin, sterol, cholic acid, desoxycholic acid and the like. The emulsifier is used in a ratio of preferably from 0.01 to 5% by weight, and more preferably from 0.1 to 3% by weight in the liquid food.

To the liquid food of the present embodiment, other sugar, a dietary fiber, a lipid, a peptide, an amino acid or a protein can be added, and further optionally a substance which has other functional properties, such as lactic acid bacteria, vitamin or mineral.

It is preferable that the liquid food of the present embodiment is ingested in an amount of from 1 to 70 g, and more preferably from 5 to 20 g per day per adult from the viewpoint of sufficiently obtaining the desired effects. Here, since there are individual differences (kinds or degree of symptoms, age and the like), the amount of the liquid food to be ingested in the present embodiment is not limited to the above range, and the amount may be properly set specifically in each case, so as to obtain the desired effects of the present embodiment.

The present embodiment further provides a method of use of the above-mentioned liquid food for preventing, ameliorating or treating a bowel disease, especially an inflammatory bowel disease. The present embodiment further provides a method for preventing, ameliorating or treating a bowel disease, especially an inflammatory bowel disease, using the above-mentioned liquid food.

Furthermore, a third embodiment of the present invention will be explained.

One of the great features of the composition for preventing, ameliorating or treating an irritable bowel syndrome of the present embodiment resides in that the composition comprises galactomannan.

The present embodiment is based on the findings of the present inventors that galactomannan, which is known to confer preferred physical properties to various industrially manufactured articles, surprisingly has an effect of preventing, ameliorating or treating an irritable bowel syndrome.

The irritable bowel syndrome can be classified into three types: diarrhea type, constipation type and alternation type. The symptom of diarrhea type is diarrhea that persistently occurs three or more times a day, accompanying an abdominal pain. The symptom of constipation type is persistent constipation accompanying an abdominal pain; and the symptom of alternation type is alternate repeat of diarrhea and constipation, wherein diarrhea accompanying an abdominal pain lasts for several days and subsequently constipation accompanying an abdominal pain begins. In addition, a patient who has not suffered from an irritable bowel syndrome but frequently experiences hypogastric pain has a potential of onset of an irritable bowel syndrome. The composition of the present embodiment can not only prevent, ameliorate or treat an irritable bowel syndrome, but also ameliorate frequently experienced hypogastric pain.

Furthermore, since the composition of the present embodiment comprises components used as a food, the composition has hardly any toxicity.

The galactomannan contained in the composition of the present embodiment is similar to the galactomannan in the first embodiment.

The composition of the present embodiment can also contain other components, so far as the desired effects of the present embodiment are not inhibited. The component includes, but not limited particularly to, for example, water (for example, tap water, distilled water, ion-exchanged water and the like), a protein, an amino acid, a peptide, a dietary fiber, a tea extract (for example, polyphenol), dextrin and the like.

The composition of the present embodiment is composed of galactomannan, or further contains other component described above, as desired. The content of the galactomannan is preferably from 0.1 to 100% by weight of the composition. The other component may be properly contained within the range that does not inhibit the desired effects of the present embodiment.

Furthermore, the form of the composition of the present embodiment may be, but not limited particularly to, a powder, a tablet, an emulsion, a liquid or the like, so far as the desired effects of the present embodiment are not inhibited.

The composition of the present embodiment can be prepared by mixing each of the above-mentioned components according to a known method (for example, a method employed in the food industry). Upon the preparation, the composition can also be properly take any form.

It is preferable that the composition of the present embodiment is continuously ingested in an amount of preferably from 1 to 70 g, and more preferably from 5 to 20 g per day per adult, from the viewpoint of suppression and treatment of an irritable bowel syndrome.

The present embodiment further provides a medicament or a food, each comprising the composition of the present embodiment.

The form of the medicament or the food of the present embodiment is similar to that in the above-mentioned first embodiment, and the method for preparing the medicament or the food is similar to that in the above-mentioned first embodiment.

The dose of the medicament for obtaining the desired effects of the present embodiment is such that a composition for ameliorating an irritable bowel syndrome is preferably from 1,000 to 70,000 mg/day, and more preferably from 5,000 to 20,000 mg/day. Here, since there are individual differences (kinds or degree of symptoms, age or the like), the dose in the present embodiment is not limited only to the above range, and the amount may be properly set specifically in each case, so as to obtain the desired effects of the present embodiment.

The content of the above-mentioned composition in the food of the present embodiment is not limited particularly, and the content is preferably from 0.1 to 100% by weight, and more preferably from 1 to 50% by weight, from the viewpoint of ease in ingestion and the effects.

The present embodiment further provides a method of use of the above-mentioned composition, medicament or food for preventing, ameliorating or treating an irritable bowel syndrome. The present embodiment further provides a method for preventing, ameliorating or treating an irritable bowel syndrome, using the above-mentioned composition, medicament or food.

EXAMPLES

The present invention will be described more specifically by means of Examples, but the present invention is by no means limited to those described herein.

Test Example 1-1

BALB/c mice (4-week old, male) were used and subjected to pre-breeding with a standard feed comprising an ordinary cornstarch (which may be hereinafter simply referred to as CS in some cases) as a carbohydrate source for one week. Individuals not showing abnormality were selected and divided into groups of 10 mice each, and each group was subjected to a test. Here, as test materials, SUNFIBER (manufactured by Taiyo Kagaku Co., Ltd.) was used as galactomannan (which may be hereinafter simply referred to as SF in some cases), and ARABINOGALACTAN LF (manufactured by Taiyo Kagaku Co., Ltd.) was used as arabinogalactan (which may be hereinafter simply referred to as AG in some cases). A 8% dextran sulfate sodium (DSS) solution was given to the above rats to induce colitis. Here, the group without the treatment was administered with physiological saline alone in place of DSS.

From the next day of the administration of DSS, a testing feed to which each material in a concentration of 5% by weight or 10% by weight was added was allowed to be taken ad libitum together with water. Here, the standard feed was given to the group without the treatment. The composition of the standard feed and the test feeds is shown in Table 1. "%"s in Table 1 all express "% by weight."

Each specimen was sacrificed after one week from the administration with DSS, and the disease activity index (weight loss: 0-4; stool consistency: 0, 2, 4; rectal ulcer: 0, 2, 4), and the amount of whole myeloperoxidase (MPO) activity in the large intestine tissue serving an index for inflammation, and TNF-α activity were evaluated for each specimen.

Figure 2:
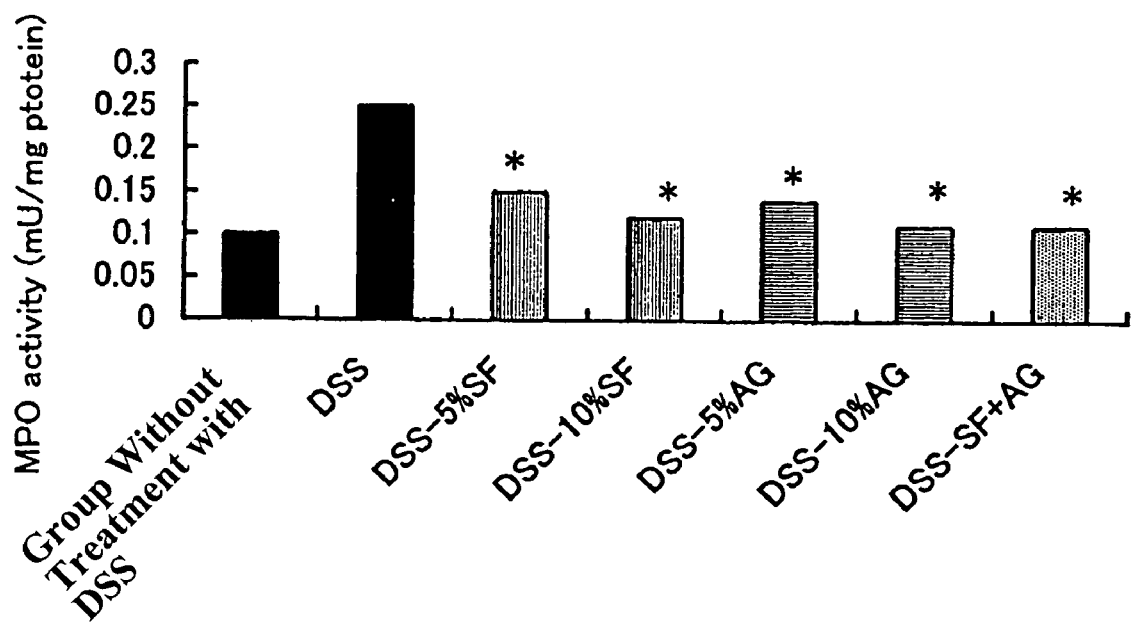
FIG. 2 is a graph showing comparison of MPO activity in total large intestine tissue in each feed group.
Figure 3:
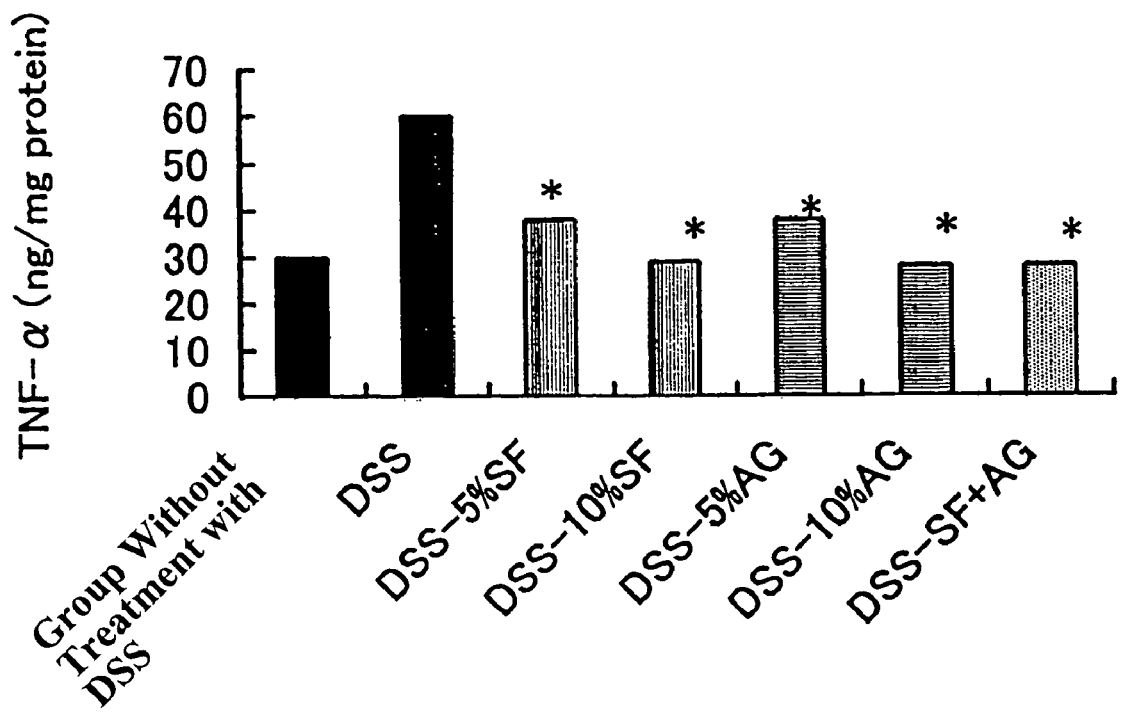
FIG. 3 is a graph showing comparison of TNF-α activity in each feed group.

(1) Ameliorative effects were found in the groups with test feed (p<0.05) as shown in FIG. 1 (Disease activity index).
(2) The MPO activity in the entire large intestine tissue, serving as an inflammation marker, showed low values in all the groups with 10% by weight test feed and the group with the SF+AG test feed (about 50% reduction from that of the DSS group, p <0.05), except for the group without the treatment with DSS as shown in FIG. 2. In addition, the activities were found to be lowered by about 40% (p <0.05) in all the groups with 5% by weight test feed.
(3) TNF-α activities, serving as an inflammatory cytokine, showed low values in all the groups with 10% by weight test feed and the group SF+AG test feed (about 50% reduction from the DSS group, p <0.05), except for the group without the treatment with DSS as shown in FIG. 3. In addition, the activities were found to be lowered by about 35% (p<0.05) in all the groups with 5% by weight test feed.

It was clarified from these experimental results that galactomannan and arabinogalactan not only show histologically ameliorative actions for inflammatory bowel diseases, but also have suppressing actions on inflammation, lowering actions on the MPO activity and the TNF-α activity which can serve as diagnostic markers in the inflammatory bowel diseases.

Test Example 1-2

Thirty patients with inflammatory bowel disease were orally administered with SF or AG in a dose of 30 g/day, 10 g per dose, for consecutive 28 days. The results of clinical symptoms (symptoms such as diarrhea, mucous and bloody stool (loose stool containing blood, mucus, and pus), fever, or weight loss) and endoscopic findings are shown in Table 2.

TABLE 1

|  | Standard Feed (CS) | 5% Test Feed (5% SF) | 10% Test Feed (10% SF) | 5% Test Feed (5% AG) | 10% Test Feed (10% AG) | 10% Test Feed (5% SF + 5% AG) |
|---|---|---|---|---|---|---|
| Cornstarch (CS)(g) | 65.5 | 60.5 | 55.5 | 60.5 | 55.5 | 55.5 |
| Galactomannan (SF)(g) | — | 5 | 10 | — | — | 5 |
| Arabinogalactan (AG)(g) | — | — | — | 5 | 10 | 5 |
| Casein (g) | 25 | 25 | 25 | 25 | 25 | 25 |
| Corn Oil (g) | 5 | 5 | 5 | 5 | 5 | 5 |
| Vitamin Mixture (g) | 1 | 1 | 1 | 1 | 1 | 1 |
| Mineral Mixture (g) | 3.5 | 3.5 | 3.5 | 3.5 | 3.5 | 3.5 |

TABLE 2

|  | SF | AG |
|---|---|---|
| Number of individuals in which amelioration in clinical symptoms and endoscopic findings were found | 26 | 25 |
| Number of individuals in which amelioration in clinical symptoms and endoscopic findings were not found | 4 | 5 |

As shown in Table 2 that amelioration in clinical symptoms and endoscopic findings of the inflammatory bowel disease was found to be ameliorated by intake of galactomannan or arabinogalactan.

Test Example 1-3

Two kinds of biscuits, each having the composition as shown in Table 3, and containing substantially the same amount of a hardly digestible component obtained by a total dietary fiber quantification method, were prepared according to an ordinary method. The resulting biscuits were subjected to a sensory test by subjects of 10 panelists. Test items were four items of color, flavor, smell and palatability, and the preferable one was selected for each item. Thereafter, examination was carried out on the basis of the examination table for two-point taste test. Here, the dietary fiber (which may be hereinafter simply referred to as DF in some cases) content was calculated from Japan Dietary Fiber Component Table (edited by Division of Science and Technology, Resource Research Association).

TABLE 3

|  | Control Group | DF Content (g) | Test Group (g) | DF Content (g) |
|---|---|---|---|---|
| Wheat Bran (g) | 26 | 13(50%) | — | — |
| Cake Flour (g) | 124 | 3.35(2.7%) | 119 | 3.1(2.6%) |
| SF(g) | — | — | 15 | 13.3(88.7%) |
| Butter (g) | 40 | — | 40 | — |
| Sugar (g) | 75 | — | 75 | — |
| Whole Egg (g) | 50 | — | 50 | — |
| Cow's Milk (g) | 10 | — | 10 | — |
| Total (g) | 335 | 16.35(4.88%) | 309 | 16.3(5.28%) |

The obtained test results are shown in Table 4. As shown in Table 4, no difference was found between the biscuit containing galactomannan and the control group in color, smell, flavor and mouth feel.

TABLE 4

| Test Item | Control Group | Test Group |
|---|---|---|
| Color | 5 | 5 |
| Smell | 5 | 5 |
| Flavor | 5 | 5 |
| Mouth Feel | 5 | 5 |

Example 1-1

Five grams of galactomannan, 93.5 g of powdered sugar, 1.0 g of gum arabic, 0.5 g of magnesium stearate, and a proper amount of flavor were kneaded in the ratio, the kneaded mixture was dried, and thereafter the dried product was tabletted, to give 100 g of a manufactured article of a tablet sweet useful for prevention or treatment of an inflammatory bowel disease.

Example 1-2

The amount 95.0 g of low fat milk was added to 5 g of galactomannan powder, to give 100 g of a manufactured article of a lactic drink useful for prevention or treatment of an inflammatory bowel disease.

Example 1-3

The amount 40.0 g of peach puree, 10.0 g of high fructose corn syrup, 0.1 g of citric acid, 0.03 g of vitamin C, a proper amount of flavor, and 46.8 g of water were added to 3.0 g of galactomannan powder, to give 100 g of a manufactured article of a refreshing drink useful for prevention or treatment of an inflammatory bowel disease.

Example 1-4

The amount 5.0 g of galactomannan powder, 51.0 g of strong flour, 15.0 g of sugar, 7.0 g of table salt, 8.0 g of an yeast, 1.0 g of an yeast, 10.0 g of butter, and 30.0 g of water were blended, and 110 g of a manufactured article of a bread loaf useful for prevention or treatment of an inflammatory bowel disease was obtained therefrom, utilizing a bread-baking oven.

Example 1-5

The amount 4.0 g of galactomannan powder, 30.0 g of granulated sugar, 35.0 g of glucose syrup, 1.0 g of pectin, 2.0 g of ⅕ apple fruit juice, and 28.0 g of water were mixed, and the mixture was heated to 85° C., and then cooled to 50° C., to give 100 g of a manufactured article of jelly useful for prevention or treatment of an inflammatory bowel disease.

Example 1-6

The amount 4.0 g of arabinogalactan powder, 30.0 g of granulated sugar, 35.0 g of glucose syrup, 1.0 g of pectin, 2.0 g of ⅕ apple fruit juice, and 28.0 g of water were mixed, and the mixture was heated to 85° C., and then cooled to 50° C., to give 100 g of a manufactured article of a jelly useful for prevention or treatment of an inflammatory bowel disease.

Example 1-7

The amount 2.0 g of galactomannan powder, 2.0 g of arabinogalactan powder, 30.0 g of granulated sugar, 35.0 g of glucose syrup, 1.0 g of pectin, 2.0 g of ⅕ apple fruit juice, and 28.0 g of water were mixed, and the mixture was heated to 85° C., and then cooled to 50° C., to give 100 g of a manufactured article of a jelly useful for prevention or treatment of an inflammatory bowel disease.

Example 2-1

Each component of Composition 1 was placed in a mixer, and the components were mixed while stirring, and the mixture was homogenized with a homogenizer (condition: 300 kg/cm$^2$). The homogenate was packed in a retort pouch or a can, and sterilized (condition: 120° C., 10 to 30 minutes), to give a liquid food. The viscosity of a 0.5 (w/v) % aqueous solution of the liquid food was determined with a B-type viscometer (manufactured by TOKI SANGYO CO., LTD.) at 25° C. As a result, the viscosity was 12 mPa·s.

TABLE 5

| <Composition 1> | Weight (g) |
|---|---|
| Soy protein (trade name: NIKKA MILKY, manufactured by Nikka Oil Mills Co., Ltd.) | 20 |
| Dextrin | 10 |
| Galactomannan (trade name: SUNFIBER, manufactured by Taiyo Kagaku Co., Ltd.) | 5 |
| Calcium Lactate | 0.3 |
| Magnesium Chloride | 0.1 |
| Vitamin Mix | 0.02 |
| Egg Yolk Lecithin | 1 |
| Water | Bal. |
| Total | 100.0 |

Comparative Example 2-1

The galactomannan was excluded from the composition in Example 2-1, to give a liquid food made of a soy protein.

Comparative Example 2-2

The soy protein and the galactomannan were excluded from the composition in Example 2-1, to give a liquid food.

Test Example 2-1

Ten patients with ulcerative colitis, 10 patients with Crohn's disease, and 10 patients with Behçet disease were asked to take the liquid foods obtained in Example 2-1 and Comparative Examples 2-1 and 2-2 mentioned above, three times a day (300 mL/time) after each meal for 3 months. The symptoms after three months were evaluated according to an assessment score of IOIBD (International Organization for the Study of Inflammatory Bowel Disease), which is an assessment score for degree of activity by an international organization for the study of inflammatory bowel disease. The results are shown in Table 6.

TABLE 6

| | | Ex. 2-1 | | Comp. Ex. 2-1 | | Comp. Ex. 2-2 | |
|---|---|---|---|---|---|---|---|
| | | No. of Persons | Evaluation | No. of Persons | Evaluation | No. of Persons | Evaluation |
| Ulcerative Colitis | Remarkably Effective | 4 | ◎ | 1 | ○ | 0 | X |
| | Effective | 3 | | 4 | | 0 | |
| | Slightly Effective | 2 | | 3 | | 0 | |
| | Unchanged | 1 | | 2 | | 10 | |
| Crohn's disease | Remarkably Effective | 3 | ◎ | 1 | ○ | 0 | X |
| | Effective | 4 | | 3 | | 0 | |
| | Slightly Effective | 2 | | 4 | | 0 | |
| | Unchanged | 1 | | 2 | | 10 | |
| Bowel Behcet disease | Remarkably Effective | 3 | ◎ | 1 | ○ | 0 | X |
| | Effective | 4 | | 5 | | 0 | |
| | Slightly Effective | 3 | | 2 | | 0 | |
| | Unchanged | 0 | | 1 | | 10 | |

Evaluation Criteria
◎: The efficacy is remarkably found.
○: The efficacy is slightly found.
X: The efficacy is not found.

Example 2-2

Each component of Composition 2 was placed in a mixer, and the components were mixed while stirring. The mixture was homogenized with a homogenizer (condition: 300 kg/cm$^2$), and the homogenate was packed in a retort pouch or can, and sterilized (conditions: 120° C., 10 to 30 minutes), to give a liquid food. The viscosity of a 0.5 (w/v) % aqueous solution of the liquid food was determined with a B-type viscometer (manufactured by TOKI SANGYO CO., LTD.) at 25° C. As a result, the viscosity was 20 mPa·s.

TABLE 7

| <Composition 2> | Weight (g) |
|---|---|
| Milk protein (trade name: SMP, manufactured by Nikka Oil Mills Co., Ltd.) | 20 |
| Dextrin | 15 |
| Galactomannan (trade name: FIBERON, manufactured by DAINIPPON PHARMACEUTICAL CO., LTD. | 5 |
| Calcium Lactate | 0.3 |
| Magnesium Chloride | 0.1 |
| Vitamin Mix | 0.02 |
| Egg Yolk Lecithin | 1 |
| Water | Bal. |
| Total | 100.0 |

Comparative Example 2-4

A liquid food of milk protein was prepared excluding the galactomannan 5 from the composition in Example 2-2.

Comparative Example 2-5

A liquid food was prepared excluding the milk protein and the galactomannan from the composition in Example 2-2.

Test Example 2-2

Ten patients with ulcerative colitis, 10 patients with Crohn's disease, and 10 patients with Behçet disease that were given the liquid foods obtained in Example 2-2 and Comparative Examples 2-4 and 2-5 mentioned above were evaluated in the same manner as in Test Example 2-1. The results are shown in Table 8.

TABLE 8

|  |  | Ex. 2-2 | | Comp. Ex. 2-4 | | Comp. Ex. 2-5 | |
| --- | --- | --- | --- | --- | --- | --- | --- |
|  |  | No. of Persons | Evaluation | No. of Persons | Evaluation | No. of Persons | Evaluation |
| Ulcerative Colitis | Remarkably Effective | 4 | ◎ | 1 | ○ | 0 | X |
|  | Effective | 3 |  | 3 |  | 0 |  |
|  | Slightly Effective | 3 |  | 4 |  | 0 |  |
|  | Unchanged | 0 |  | 2 |  | 10 |  |
| Crohn's disease | Remarkably Effective | 3 | ◎ | 0 | ○ | 0 | X |
|  | Effective | 5 |  | 4 |  | 0 |  |
|  | Slightly Effective | 1 |  | 4 |  | 0 |  |
|  | Unchanged | 1 |  | 2 |  | 10 |  |
| Bowel Behcet disease | Remarkably Effective | 2 | ◎ | 1 | ○ | 0 | X |
|  | Effective | 5 |  | 5 |  | 0 |  |
|  | Slightly Effective | 2 |  | 2 |  | 0 |  |
|  | Unchanged | 1 |  | 1 |  | 10 |  |

Evaluation Criteria
◎: The efficacy is remarkably found.
○: The efficacy is slightly found.
X: The efficacy is not found.

Example 2-3

Each component of Composition 3 was placed in a mixer, and the components were mixed while stirring. The mixture was homogenized with a homogenizer (condition: 300 kg/cm$^2$), and the homogenate was packed in a retort pouch or can, and sterilized (conditions: 120° C., 10 to 30 minutes), to give a liquid food. The viscosity of a 0.5 (w/v) % aqueous solution of the liquid food was determined with a B-type viscometer (manufactured by TOKI SANGYO CO., LTD.) at 25° C. As a result, the viscosity was 18 mPa·s.

TABLE 9

| <Composition 3> | Weight (g) |
| --- | --- |
| Degraded soy protein (trade name: Amino 1000, manufactured by GNC) | 20 |
| Dextrin | 15 |
| Arabinogalactan (trade name: ARABINOGALACTAN LF, manufactured by Taiyo Kagaku Co., Ltd.) | 5 |
| Calcium Lactate | 0.3 |
| Magnesium Chloride | 0.1 |
| Vitamin Mix | 0.02 |
| Egg Yolk Lecithin | 1 |
| Water | Bal. |
| Total | 100.0 |

Comparative Example 2-6

A liquid food of milk protein was prepared excluding the arabinogalactan from the composition in Example 2-3.

Comparative Example 2-7

A liquid food was prepared excluding the degraded soy protein and the arabinogalactan from the composition in Example 2-3.

Test Example 2-3

Ten patients with ulcerative colitis, 10 patients with Crohn's disease, and 10 patients with Behçet disease that were given the liquid foods obtained in Example 2-3 and Comparative Examples 2-6 and 2-7 mentioned above were evaluated in the same manner as in Test Example 2-1. The results are shown in Table 10.

TABLE 10

| | | Ex. 2-3 No. of Persons | Ex. 2-3 Evaluation | Comp. Ex. 2-6 No. of Persons | Comp. Ex. 2-6 Evaluation | Comp. Ex. 2-7 No. of Persons | Comp. Ex. 2-7 Evaluation |
|---|---|---|---|---|---|---|---|
| Ulcerative Colitis | Remarkably Effective | 4 | ◎ | 1 | ○ | 0 | X |
| | Effective | 3 | | 4 | | 0 | |
| | Slightly Effective | 1 | | 3 | | 0 | |
| | Unchanged | 2 | | 2 | | 10 | |
| Crohn's disease | Remarkably Effective | 3 | ◎ | 1 | ○ | 0 | X |
| | Effective | 4 | | 3 | | 0 | |
| | Slightly Effective | 1 | | 4 | | 0 | |
| | Unchanged | 2 | | 2 | | 10 | |
| Bowel Behcet disease | Remarkably Effective | 2 | ◎ | 1 | ○ | 0 | X |
| | Effective | 5 | | 5 | | 0 | |
| | Slightly Effective | 1 | | 2 | | 0 | |
| | Unchanged | 2 | | 1 | | 10 | |

Evaluation Criteria
◎: The efficacy is remarkably found.
○: The efficacy is slightly found.
X: The efficacy is not found.

Example 2-4

Each component of Composition 4 was placed in a mixer, and the components were mixed while stirring. The mixture was homogenized with a homogenizer (condition: 300 kg/cm$^2$), and the homogenate was packed in a retort pouch or can, and sterilized (conditions: 120° C., 10 to 30 minutes), to give a liquid food. The viscosity of a 0.5 (w/v) % aqueous solution of the liquid food was determined with a B-type viscometer (manufactured by TOKI SANGYO CO., LTD.) at 25° C. As a result, the viscosity was 30 mPa·s.

TABLE 11

| <Composition 4> | Weight (g) |
|---|---|
| Degraded soy protein (trade name: Amino 1000, manufactured by GNC) | 20 |
| Dextrin | 10 |
| Arabinogalactan (trade name: ARABINOGALACTAN LF, manufactured by Taiyo Kagaku Co., Ltd.) | 5 |
| Galactomannan (trade name: SUNFIBER, manufactured by Taiyo Kagaku Co., Ltd.) | 5 |
| Calcium Lactate | 0.3 |
| Magnesium Chloride | 0.1 |
| Vitamin Mix | 0.02 |
| Egg Yolk Lecithin | 1 |
| Water | Bal. |
| Total | 100.0 |

Comparative Example 2-8

A liquid food of milk protein was prepared excluding the galactomannan and the arabinogalactan from the composition in Example 2-4.

Comparative Example 2-9

A liquid food was prepared excluding the degraded soy protein and the galactomannan from the composition in Example 2-4.

Test Example 2-4

Ten patients with ulcerative colitis, 10 patients with Crohn's disease, and 10 patients with Behçet disease that were given the liquid foods obtained in Example 2-4 and Comparative Examples 2-8 and 2-9 mentioned above were evaluated in the same manner as in Test Example 2-1. The results are shown in Table 12.

TABLE 12

| | | Ex. 2-4 No. of Persons | Ex. 2-4 Evaluation | Comp. Ex. 2-8 No. of Persons | Comp. Ex. 2-8 Evaluation | Comp. Ex. 2-9 No. of Persons | Comp. Ex. 2-9 Evaluation |
|---|---|---|---|---|---|---|---|
| Ulcerative Colitis | Remarkably Effective | 4 | ◎ | 2 | ○ | 0 | X |
| | Effective | 3 | | 2 | | 0 | |
| | Slightly | 3 | | 4 | | 0 | |

TABLE 12-continued

| | | Ex. 2-4 | | Comp. Ex. 2-8 | | Comp. Ex. 2-9 | |
|---|---|---|---|---|---|---|---|
| | | No. of Persons | Evaluation | No. of Persons | Evaluation | No. of Persons | Evaluation |
| Crohn's disease | Effective | | | | | | |
| | Unchanged | 0 | | 2 | | 10 | |
| | Remarkably Effective | 4 | ◎ | 1 | ○ | 0 | X |
| | Effective | 4 | | 3 | | 0 | |
| | Slightly Effective | 1 | | 4 | | 0 | |
| Bowel Behcet disease | Unchanged | 1 | | 2 | | 10 | |
| | Remarkably Effective | 2 | ◎ | 0 | ○ | 0 | X |
| | Effective | 5 | | 5 | | 0 | |
| | Slightly Effective | 2 | | 4 | | 0 | |
| | Unchanged | 1 | | 1 | | 10 | |

Evaluation Criteria
◎: The efficacy is remarkably found.
○: The efficacy is slightly found.
X: The efficacy is not found.

From the results of Tables 6, 8, 10 and 12, it was confirmed that the liquid foods of Examples 2-1 to 2-4 exhibit excellent effects for patients with ulcerative colitis, Crohn's disease, and bowel Behçet disease. On the other hand, the liquid foods of Comparative Examples 2-1, 2-3, 2-4, 2-6 and 2-8 are found to show slight efficacy for patients with ulcerative colitis, Crohn's disease, and bowel Behçet disease, and the liquid foods of Comparative Examples 2-2, 2-5, 2-7, and 2-9 are not found to show any efficacy for any one of the patients. Here, no adverse actions were found in this test at all.

Example 3-1

A 0.1 N hydrochloric acid was added to 900 g of water, to adjust the pH of the solution to 4.5. Thereto were added 0.2 g of β-mannanase derived from a bacterium belonging to the genus *Aspergillus* (manufactured by Novo Nordisk Bioindustry, Ltd.) and 100 g of guar gum powder (manufactured by Taiyo Kagaku Co., Ltd., trade name: G-1, high-grade product), and the mixture was mixed to carry out enzymolysis of guar gum at 40° to 45° C. over a period of 24 hours. After the reaction, the mixture was heated at 90° C. for 15 minutes to deactivate the enzyme. The mixture was subjected to filter separation (suction filtration) to remove insoluble substances, to give a transparent solution. The transparent solution was concentrated under a reduced pressure (evaporator manufactured by Yamato) (solid content: 20% by weight), and the concentrate was dried with a spray-drier (manufactured by Ohkawara Kakohki Co., Ltd.), to give 65 g of a composition of the present invention (content of degraded galactomannan: 100% by weight) in the form of powder.

The viscosity of a 0.5 (w/v) % aqueous solution prepared by dissolving the composition in water was determined with a B-type viscometer (manufactured by TOKI SANGYO CO., LTD.) at 25° C. As a result, the viscosity was 2 mPa·s. In addition, the aqueous solution was subjected to high-performance liquid chromatography (column: YMC-Pack Diol-120, manufactured by YMC) using polyethylene glycols (molecular weights: 2,000, 20,000 and 200,000) as molecular weight markers to determine its average molecular weight. As a result, the average molecular weight was about 20,000.

Example 3-2

A 0.1 N hydrochloric acid was added to 900 g of water, to adjust the pH of the solution to 3. Thereto were added 0.15 g of β-mannase derived from a bacterium belonging to the genus *Aspergillus* (manufactured by Novo Nordisk Industry, Ltd.) and 100 g of guar gum powder (manufactured by Taiyo Kagaku Co., Ltd., trade name: G-2, medium-grade product), and the mixture was mixed to carry out enzymolysis of guar gum at 40° to 45° C. over a period of 24 hours. After the reaction, the mixture was heated at 90° C. for 15 minutes to deactivate the enzyme. The mixture was subjected to filter separation (suction filtration) to remove insoluble substances, to give a transparent solution. The transparent solution was concentrated under a reduced pressure (evaporator manufactured by Yamato) (solid content: 20% by weight), and the concentrate was dried with a spray-drier (manufactured by Ohkawara Kakohki), to give 68 g of a composition of the present invention (content of degraded galactomannan: 100% by weight) in the form of powder.

The viscosity for the composition obtained was determined in the same manner as in Example 3-1. As a result, the viscosity was 3 mPa·s. In addition, its average molecular weight was determined. As a result, the average molecular weight was about 25,000.

Example 3-3

A 0.1 N hydrochloric acid was added to 900 g of water, to adjust the pH of the solution to 4. Thereto were added 0.25 g of β-mannase derived from a bacterium belonging to the genus *Aspergillus* (manufactured by Novo Nordisk Industry, Ltd.) and 100 g of guar gum powder (manufactured by Taiyo Kagaku Co., Ltd., trade name: G-3, low-grade product), and the mixture was mixed to carry out enzymolysis of guar gum at 50° to 55° C. over a period of 12 hours. After the reaction, the mixture was heated at 90° C. for 15 minutes to deactivate the enzyme. The mixture was subjected to filter separation (suction filtration) to remove insoluble substances, to give a transparent solution. The transparent solution was concentrated under a reduced pressure (evaporator manufactured by Yamato) (solid content: 20% by weight), and dextrin was added to the concentrate in an amount of one-quarter the weight of the solid content, to dissolve. The solution obtained was dried with a spray-drier (manufactured by Ohkawara Kakohki), to give 80 g of a composition of the present invention (content of degraded galactomannan: 75% by weight) in the form of powder.

The viscosity for the degraded galactomannan before addition of dextrin was determined in the same manner as in Example 3-1. As a result, the viscosity was 1 mPa·s. In addition, its average molecular weight was determined. As a result, the average molecular weight was about 15,000.

Test Example 3-1

Ninety patients with an irritable bowel syndrome (diarrhea type) were divided into three groups of 30 persons each. A first group was orally administered with the composition prepared in Example 3-1 in an amount of 5 g/day, a second group was orally administered with the composition prepared in Example 3-1 in an amount of 10 g/day, and a third group was orally administered with wheat bran in an amount of 5 g/day, each group being administered for 12 weeks. After the termination of administration, the ratio of amelioration in the symptoms was examined. The results are shown in Table 13.

TABLE 13

|  | Ratio of Amelioration* |
| --- | --- |
| First Group | 80% |
| Second Group | 83% |
| Third Group | 2% |

*Ratio of amelioration = Number of persons showing ameliorated symptoms/30 × 100

From the results of Table 13, the amelioration of the irritable bowel syndrome (diarrhea type) was found by the administration of the composition of the present invention.

Test Example 3-2

Ninety patients with an irritable bowel syndrome (constipation type) were divided into three groups of 30 persons each. A first group was orally administered with the composition prepared in Example 3-1 in an amount of 5 g/day, a second group was orally administered with the composition prepared in Example 3-1 in an amount of 10 g/day, and a third group was orally administered with wheat bran in an amount of 5 g/day, each group being administered for 12 weeks. After the termination of administration, the ratio of amelioration of the symptoms was examined. The results are shown in Table 14.

TABLE 14

|  | Ratio of Amelioration* |
| --- | --- |
| First Group | 83% |
| Second Group | 90% |
| Third Group | 3% |

*Ratio of amelioration = Number of persons showing ameliorated symptoms/30 × 100

From the results of Table 14, the amelioration of the irritable bowel syndrome (constipation type) was found by the administration of the composition of the present invention.

Test Example 3-3

Ninety patients with an irritable bowel syndrome (alternation type) were divided into three groups of 30 persons each. A first group was orally administered with the composition prepared in Example 3-1 in an amount of 5 g/day, a second group was orally administered with the composition prepared in Example 3-1 in an amount of 10 g/day, and a third group was orally administered with wheat bran in an amount of 5 g/day, each group being administered for 12 weeks. After the termination of administration, the ratio of amelioration of the symptoms was examined. The results are shown in Table 15.

TABLE 15

|  | Ratio of Amelioration* |
| --- | --- |
| First Group | 80% |
| Second Group | 83% |
| Third Group | 3% |

*Ratio of amelioration = Number of persons showing ameliorated symptoms/30 × 100

From the results of Table 15, the amelioration of the irritable bowel syndrome (alternation type) was found by the administration of the composition of the present invention.

Test Example 3-4

Ninety patients who were suspected of developing an irritable bowel syndrome (patients suffering from frequent cramps in the lower abdomen) were divided into three groups of 30 persons each. A first group was orally administered with the composition prepared in Example 3-1 in an amount of 5 g/day, a second group was orally administered with the composition prepared in Example 3-1 in an amount of 10 g/day, and a third group was orally administered with wheat bran in an amount of 5 g/day, each group being administered for 12 weeks. After the termination of each administration, the ratio of amelioration of the symptoms was examined. The results are shown in Table 16.

TABLE 16

|  | Ratio of Amelioration* |
| --- | --- |
| First Group | 90% |
| Second Group | 97% |
| Third Group | 2% |

*Ratio of amelioration = Number of persons showing ameliorated symptoms/30 × 100

From the results of Table 16, the amelioration of the cramps in the lower abdomen was found by the administration of the composition of the present invention.

| Application Example 3-1 Tablet Sweet | |
| --- | --- |
| Powdered sugar | 93.5% by weight |
| Gum arabic | 1.0% by weight |
| Stearic acid | 0.5% by weight |
| Flavor | Proper amount |
| Galactomannan (SUNFIBER, manufactured by Taiyo Kagaku Co., Ltd.) | 5.0% by weight |
| Application Example 3-2 Custard Pudding | |
| Whole egg | 20.0% by weight |
| Cow's Milk | 70.0% by weight |
| Sugar | 8.0% by weight |
| Vanilla Flavor | Proper amount |
| Brandy | Proper amount |
| Galactomannan (SUNFIBER, manufactured by Taiyo Kagaku Co., Ltd.) | 2.0% by weight |
| Application Example 3-3 Udon | |
| Strong flour | 40 g |
| Cake flour | 152 g |
| Galactomannan (SUNFIBER, manufactured by Taiyo Kagaku Co., Ltd.) | 8 g |

| | |
|---|---|
| Table Salt | 4 g |
| Water | 68 g |
| Application Example 3-4 French Dressing | |
| Vegetable oil | 35.0% by weight |
| Sugar | 9% by weight |
| Galactomannan (SUNFIBER, manufactured by Taiyo Kagaku Co., Ltd.) | 5% by weight |
| Edible Vinegar | 16.0% by weight |
| Table Salt | 4% by weight |
| Mustard | 1.2% by weight |
| Seasoning | Proper amount |
| Xanthan gum | 0.3% by weight |
| Water | 5% by weight |

INDUSTRIAL APPLICABILITY

Galactomannan and arabinogalactan, as mentioned above, clearly have an effect of preventing, ameliorating or treating a bowel disease, particularly an inflammatory bowel disease. By ingesting a composition prepared by formulating the galactomannan and the arabinogalactan into other food materials in various forms of foods, the inflammatory bowel disease, particularly chronic inflammatory disease can be prevented, ameliorated or treated. In addition, since the galactomannan and the arabinogalactan have favorable color, odor, taste, and palatability, the food formulated therewith can be ingested in the same manner as in an ordinary food, whereby the galactomannan and the arabinogalactan can be ingested over a long period of time. The present invention provides a liquid food capable of efficiently preventing, ameliorating or treating the inflammatory bowel disease by a combined use of a protein with galactomannan and/or arabinogalactan. In addition, according to the present invention, the galactomannan can be utilized for prevention, amelioration or treatment of an irritable bowel syndrome.

The invention claimed is:

1. A method for ameliorating or treating an inflammatory bowel disease, comprising
administering a composition comprising galactomannan in an amount sufficient to lower the activity of myeloperoxidase and TNF-α to a patient suffering from said inflammatory bowel disease, wherein said galactomannan is a degraded galactomannan having an average molecular weight of from 8,000 to 50,000 and a viscosity of 10 mPa·s or less, as determined by 0.5(w/v) % aqueous solution of the degraded galactomannan,
wherein the degraded galactomannan is produced by hydrolyzing guar gum with β-mannanase. without further chemical processing, and
wherein the administering step includes administering the composition having 5-100% by weight of galactomannan in an amount of 1 to 70g/day/adult.

2. The method according to claim 1, wherein said galactomannan is administered with a protein.

3. The method according to claim 2, wherein the protein is one or more proteins selected from the group consisting of a soy protein, a milk protein, a yolk protein, an albumen protein, a wheat protein and a degraded product thereof.

4. The method according to claim 2, wherein said composition is administered as a liquid food.

5. The method according to claim 1, wherein said inflammatory bowel disease is selected from the group consisting of ulcerative colitis, Crohn's disease and intestinal Behçet disease.

6. The method according to claim 2, wherein said inflammatory bowel disease is selected from the group consisting of ulcerative colitis, Crohn's disease and intestinal Behcet disease.

7. The method according to claim 1, wherein said composition comprises galactomannan and does not comprise arabinogalactan.

8. The method according to claim 1, wherein the degraded galactomannan is produced by a process consisting essentially of hydrolyzing guar gum with β-mannanase.

9. The method according to claim 1, wherein β-mannanase is drived from a bacterium belonging to *Aspergillus* or *Rhizopus*.

10. The method according to claim 1, wherein hydrolyzing guar gum with β-mannanase is carried out at a temperature of 10 to 80° C. for about 1 to about 75 hours.

11. The method according to claim 1, wherein β-mannanase for hydrolyzing the guar gum is used in an amount of 0.1 to 20 parts by weight based on 100 parts by weight of guar gum.

* * * * *